United States Patent
Oluseyi et al.

(10) Patent No.: US 6,633,391 B1
(45) Date of Patent: Oct. 14, 2003

(54) MONITORING OF FILM CHARACTERISTICS DURING PLASMA-BASED SEMI-CONDUCTOR PROCESSING USING OPTICAL EMISSION SPECTROSCOPY

(75) Inventors: Hakeem Oluseyi, Stanford, CA (US); Moshe Sarfaty, Cupertino, CA (US)

(73) Assignee: Applied Materials, Inc, Santa Clara, CA (US)

( * ) Notice: Subject to any disclaimer, the term of this patent is extended or adjusted under 35 U.S.C. 154(b) by 33 days.

(21) Appl. No.: 09/708,258

(22) Filed: Nov. 7, 2000

(51) Int. Cl.[7] ............ G01N 21/73; H01J 37/32

(52) U.S. Cl. ............ 356/630; 356/632

(58) Field of Search ............ 356/630, 632, 356/503, 32; 250/340, 341.4; 204/192.13

(56) References Cited

U.S. PATENT DOCUMENTS

| | | |
|---|---|---|
| 4,208,240 A | 6/1980 | Latos |
| 4,707,611 A | 11/1987 | Southwell |
| 4,776,695 A | 10/1988 | van Pham et al. |
| 5,048,960 A | 9/1991 | Hayashi et al. |
| 5,160,402 A | 11/1992 | Cheng |
| 5,270,222 A | 12/1993 | Moslehi |
| 5,335,066 A | 8/1994 | Yamada et al. |
| 5,374,327 A | 12/1994 | Imahashi et al. |
| 5,386,119 A | 1/1995 | Ledger |
| 5,403,433 A | 4/1995 | Morrison et al. |
| 5,493,401 A | 2/1996 | Horie et al. |
| 5,565,114 A | 10/1996 | Saito et al. |
| 5,643,364 A | 7/1997 | Zhao et al. |
| 5,658,423 A | 8/1997 | Angell et al. |
| 5,686,993 A | 11/1997 | Kokubo et al. |
| 5,694,207 A | 12/1997 | Hung et al. |
| 5,711,843 A | 1/1998 | Jahns |
| 5,719,495 A | 2/1998 | Moslehi |
| 5,877,032 A | 3/1999 | Guinn et al. |
| 5,885,472 A | 3/1999 | Miyazaki et al. |
| 5,983,906 A | 11/1999 | Zhao et al. |
| 6,046,796 A | 4/2000 | Markle et al. |
| 6,052,183 A | 4/2000 | Lee |

(List continued on next page.)

FOREIGN PATENT DOCUMENTS

| | | |
|---|---|---|
| EP | 0677737 | 10/1995 |
| EP | 0756318 | 1/1997 |
| EP | 0768701 | 4/1997 |
| EP | 0878842 | 11/1998 |
| JP | 05291188 | 5/1993 |
| JP | 10335309 | 12/1998 |

OTHER PUBLICATIONS

White et al., "Spatial Characterization of Wafer State Using Principal Component Analysis of Optical Emission Spectra in Plasma Etch", IEEE Transactions on Semiconductor Manufacturing, IEEE Inc., New York, US, vol. 10, no. 1, Feb. 1997 (1997–02), pp. 52–61, XP002924118, ISSN: 0894–6507.

*Primary Examiner*—Scott J. Sugarman
*Assistant Examiner*—Richard Hanig
(74) *Attorney, Agent, or Firm*—Ken Brooks; Joseph Bach

(57) ABSTRACT

A method and system to monitor characteristics of films by sensing the spectral emissions of a plasma to which the films are exposed. As a result, the method includes sensing optical energy produced by the plasma. The optical energy has a plurality of spectral bands associated therewith, a subset of which is identified as including information corresponding to the film characteristics. The film characteristics are then measured as a function of this information. To increase the accuracy of the measurements, in one embodiment of the present invention a subgroup of the plurality of spectral bands is observed that has data associated that is substantially independent of the characteristics of interest. The characteristics are then measured as a function of both the information and the data.

20 Claims, 11 Drawing Sheets

U.S. PATENT DOCUMENTS

| | | |
|---|---|---|
| 6,068,783 A | 5/2000 | Szetsen |
| 6,074,568 A | 6/2000 | Adachi et al. |
| 6,153,115 A | 11/2000 | Le et al. |
| 6,157,867 A | 12/2000 | Hwang et al. |
| 6,278,519 B1 | 8/2001 | Rosencwaig et al. |
| 6,278,809 B1 | 8/2001 | Johnson et al. |
| 6,297,880 B1 | 10/2001 | Rosencwaig et al. |
| 6,304,326 B1 | 10/2001 | Aspnes et al. |
| 6,419,801 B1 * | 7/2002 | Smith, Jr. et al. ....... 204/192.13 |
| 6,603,538 B1 | 8/2003 | Oluseyi et al. |

* cited by examiner

MONITORING OF FILM CHARACTERISTICS DURING PLASMA-BASED SEMI-CONDUCTOR PROCESSING USING OPTICAL EMISSION SPECTROSCOPY

BACKGROUND OF THE INVENTION

The present invention relates to monitoring of semiconductor processes. More particularly, the present invention relates to a method and system for monitoring characteristics of films exposed to a plasma in a semiconductor processing chamber.

Process control and diagnostics are important to determine the characteristics of films being deposited during semiconductor processing. For example, current process control and diagnostics of plasma enhanced deposition processes involve three techniques: optical endpoint detection, interferometric endpoint detection and test substrate measurement technique. The optical endpoint detection technique involves ascertaining a process endpoint by monitoring one or two narrow bands of optical emission from process plasmas. A drawback with this technique concerns the limited information regarding the characteristics of the films being deposited.

The interferometric endpoint technique takes advantage of interferometry to determine whether a film has obtained a predetermined thickness. Drawbacks associated with the interferometric endpoint technique include the limitations of materials that are suitable for use with interferometric measurements. Some materials, such as metals, do not show interferometric interference fringes unless the material being measured is extremely thin. Secondly, the interferometric technique does not predict true process endpoints.

The test substrate measurement technique involves direct measurement of a film disposed on a substrate. As a result, the test substrate measurement technique evaluates the last process step performed by examination of test wafers that are processed within a group of production wafers. This is a drawback, because this technique does not identify failures of intermediate process steps. This may result in the loss of a great number of process wafers. In addition, the test substrate measurement technique is destructive in nature, substantially reducing the operational life of the test substrate.

What is needed, therefore, is a non-destructive technique to monitor process conditions in a semiconductor processing chamber in real-time that accurately characterize films being deposited on a substrate.

SUMMARY OF THE INVENTION

Provided is a method and system that features monitoring characteristics of films by sensing the spectral emissions of a plasma to which the films are exposed. As a result, the method includes sensing optical energy produced by the plasma. The optical energy has a plurality of spectral bands associated therewith, a subset of which is identified as including information corresponding to the film characteristics. The film characteristics are then measured as a function of thaws information. Specifically, the intensity of the subset of spectral bands is sensed from which the film characteristics are determined. To increase the accuracy of the measurements, in one embodiment of the present invention a subgroup of the plurality of spectral bands is observed that has data associated therewith that is substantially independent of the characteristics of interest. In this manner, film characteristics are measured as a function of both the information and the data. Specifically, the intensity of the spectral bands associated with the subset and subgroup are identified and quantized, defining first and second quantizations. A ratio of the first and second quantizations is determined that attenuates information that results from degradation of the processing environment. The system includes a detector in optical communication with the processing chamber to sense optical energy generated by the plasma, and a spectrum analyzer, in electrical communication with the optical detector. The spectrum analyzer resolves the spectral bands and produces information corresponding thereto. A processor is in electrical communication with the spectrum analyzer, and a memory is in electrical communication with the processor. The memory includes a computer-readable medium having a computer-readable program embodied therein that controls the system to carry-out the method.

DETAILED DESCRIPTION OF THE INVENTION

Figure 1:
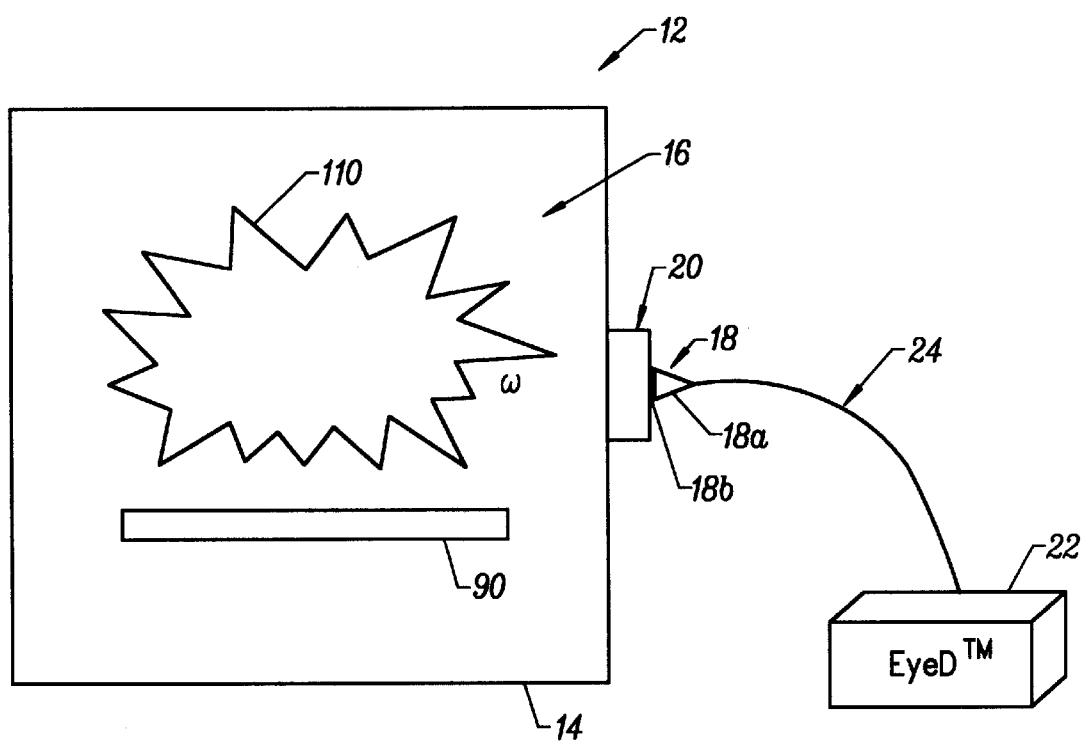
FIG. 1 is a simplified plan view of a plasma-based semiconductor processing system in accordance with the present invention.

Referring to FIG. 1, a plasma-based semiconductor processing system 12 includes a housing 14 that defines a processing chamber 16. A sensor assembly 18 is in optical communication with the processing chamber 16 via a window 20 that is typically formed from quartz and is disposed in the housing 14. A spectrum analyzer 22 is in data communication with the sensor assembly 18 via a fiber-optic cable 22. The sensor assembly 18 may include any known detector in the art, such as a charged-coupled-device (CCD) 18a and typically has a dispersive grating 18b disposed between the CCD device 18a and the window 20. In this manner, each of the pixels associated with the CCD device 18a may correspond to a set of wavelengths that differs from the set of wavelengths that the remaining pixels of the CCD device 18a are associated. An exemplary spectrum analyzer is sold under the name trade EyeD™ by Applied Materials, Inc. of Santa Clara, Calif. the assignee of the rights in the present patent application. The system 12 may be any plasma-based system known in the semiconductor art, e.g., plasma etch system, sputter deposition system and the like, for purposes of the present discussion, the system 12 will be described as a plasma enhanced chemical vapor deposition (PECVD) system.

Figure 2:
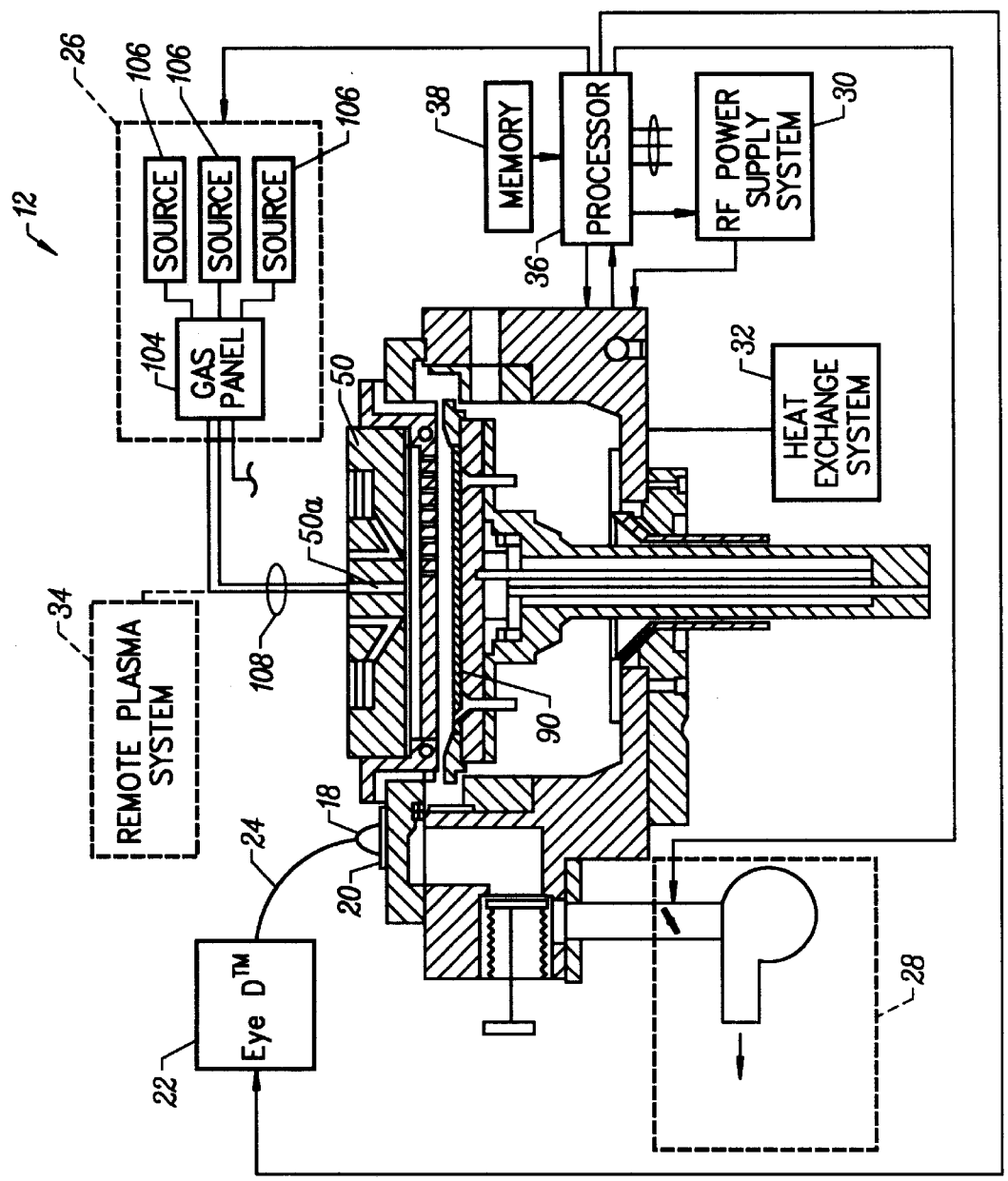
FIG. 2 is a detailed view of the semiconductor processing system, shown above in FIG. 1.

Referring to FIG. 2, the exemplary PECVD system 12 includes a gas delivery system 26, a vacuum system 28, an RF power supply system 30, a heat exchange system 32, and a remote plasma system 34 all operated under control of a processor 36. A memory 38, suitable for storing control programs, is in data communication with the processor 36. The gas delivery system 26, vacuum system 28, heat exchange system 32, and remote plasma system 34 are all in fluid communication with the processing chamber 16, discussed more fully below.

Figure 3:
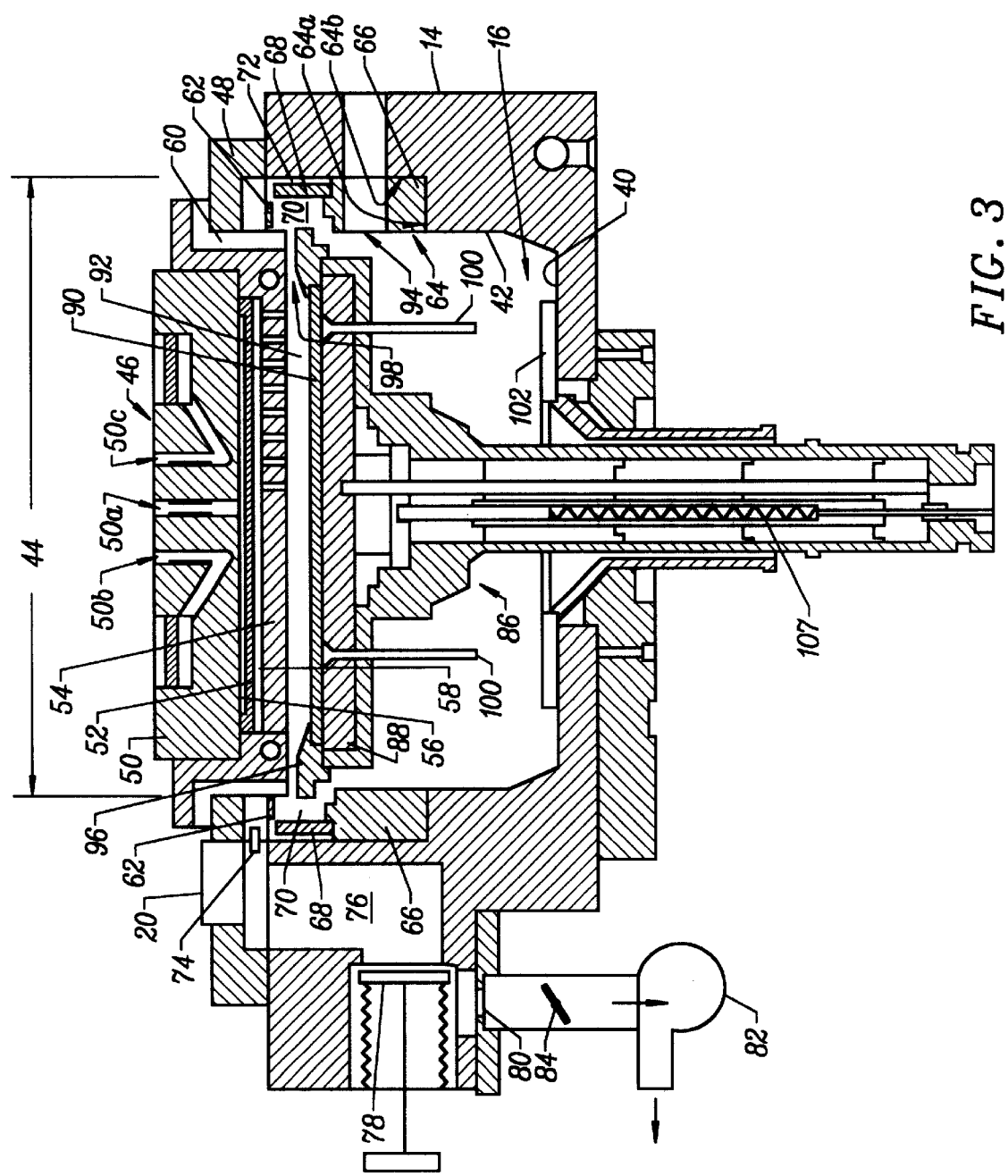
FIG. 3 is a detailed cross-sectional view of a processing chamber, shown above in FIGS. 1 and 2.

Referring to FIG. 3, housing 14 includes a base wall 40 having a sidewall 42 extending therefrom and terminating in an opening 44. A lid 46 is moveably attached to the sidewall 42 to selectively seal the opening 44. The lid 46 includes a body 48 having a throughway in which a gas-feed cover plate 50, baffle plate 52 and a showerhead 54 are disposed. The gas-feed cover plate 50 includes a plurality of throughways, shown generally as 50a–c. One of the throughways, 50a, is centrally disposed and extends completely through gas-feed the cover plate 50 between the opposing surfaces thereof. The showerhead 54 is disposed adjacent to, and spaced-apart from, the gas-feed cover plate 50. The baffle plate 52 is disposed between the gas-feed cover plate 50 and the showerhead 54. The baffle plate 52 is spaced-apart from the gas-feed cover plate 50, defining a gap 56 therebetween. The showerhead 54 is spaced-apart from the baffle plate 52, defining a space 58 therebetween. Throughways 50a–c in the baffle plate 52 place the gap 56 and the space 58 in fluid communication, and a plurality of throughways 50a–c in the showerhead 54 place the space 58 in fluid communication with the processing chamber 16. Disposed between the showerhead 54 and the body 48 is an isolator 60. A ceramic liner 62 covers a portion of the body 48 that faces the processing chamber 16.

The sidewall 42 includes an annular recess 64 having a nadir surface 64a and a side surface 64b. A ceramic ring 66 is positioned within the annular recess 64 to completely cover the nadir surface 64a and extends upwardly therefrom toward the opening 44, partially covering the side surface 64b. A wall liner 68 is positioned in the annular recess 64 to cover the remaining segment of the side surface 64b located between the opening 44 and the ceramic ring 66. In this manner, an annular pumping channel 70 is defined between the ceramic liner 62, the ceramic ring 66, the wall liner 68 and the isolator 60. The annular pumping channel 70 is located proximate to the showerhead 54. The wall liner 68 is spaced-apart from both the side surface 64b and the wall liner 68 and forms a passageway 72 between the lid 46 and the wall liner 68.

In fluid communication with the annular pumping channel 70 is an exhaust aperture 74 to place the processing chamber 16 in fluid communication with a pumping plenum 76. A valve 78, in fluid communication with the pumping plenum 76, gates the exhaust into an exhaust vent 80 from the pumping plenum 76 that occurs under vacuum produced by a vacuum pump 82. The vacuum pump 82 includes a throttle valve 84.

A pedestal 86, that may be resistively heated, is disposed within the processing chamber 16 and includes a pocket 88 adapted to receive a substrate 90, such as a semiconductor substrate. In this manner, the pedestal 86 supports the substrate 90 within the processing chamber 16. The pedestal 86 may be moved between the lid 46 and the base wall 40 to place the substrate 90 in a processing zone 92, disposed proximate to the showerhead 54, and a loading position where the pocket 88 is positioned below an access port 94 that is formed into the housing 14 and ceramic ring 66. The access port 94 can be hermetically-sealed to prevent the flow of process fluids from egressing from the processing chamber 16. The movement of the pedestal 86 may be achieved by employing a self-adjusting lift mechanism, described in detail in U.S. Pat. No. 5,951,776 to Selyutin et al., entitled "Self-Aligning Lift Mechanism", and assigned to the assignee of the present invention.

A ring 96 that may either be a clamp ring or a shadow ring, dependent upon the process, is positioned to contact a periphery of the pedestal 86 so as to surround the substrate 90 when placed in the processing zone 92. In this manner, an annular choke aperture 98 may be defined between the isolator 60 and ring 96. The ring 96 may be made of any suitable material depending upon the application, such as fused silica, titanium and the like. Were the ring 96 a shadow ring, the ring 96 is received on the ceramic ring 66 defining a space between the ring 96 and the pedestal 86, were the pedestal 86 in the loading position, i.e., retracted downwardly in the processing chamber 16. As the pedestal 86 supporting the next substrate 90 is raised into processing position, it picks up the ring 96. The position of the substrate 90 is be maintained on the pedestal 86 via vacuum chucking the substrate 90 thereto.

Were the ring 96 a clamp ring, the ring 96 would securely fasten the substrate 90 to the pedestal 86 during processing. Thus, the ring 96 would securely position substrate 90 onto the pedestal 86 in addition to, or instead of, vacuum chucking the substrate 90 thereto.

Lift pins 100 are moveably attached to the pedestal 86 so that one end of the same may engage a vertically movable lifting ring 102 positioned between the underside of the pedestal 86 and the base wall 40. The lift pins 100 extend beyond the surface of the pedestal 86 in which the substrate pocket 88 is formed when the lifting ring 102 is moved upwardly to engage the underside of the lift pins 100. Positioning of a substrate 90 with respect to the substrate pocket 88 is achieved via a robot blade (not shown) in cooperation with the lift pins 100 when the pedestal 86 is in the loading position. When the pedestal 86 is in the loading position, the substrate 90 is spaced-apart from the substrate pocket 88 allowing the robot blade access to the substrate 90. The substrate 90 is lifted from and placed onto the pedestal 86 by relative motion between the lift pins 100 and the pedestal 86. To receive the substrate into the substrate pocket 88, the pedestal 86 rises toward the processing zone 92. A suitable robotic transfer assembly is described in U.S. Pat. No. 4,951,601 to Maydan and assigned to the assignee of the present invention.

Referring again to FIG. 2, the gas delivery system 26 includes gas supply panel 104 and a plurality of fluid sources, solid sources or combination thereof, shown generally as gas source 106. The supply line for each of the process gases includes a shut-off valve (not shown) that can be used to automatically or manually shut off the flow of process fluids, Us well as a mass flow controller (not shown) that measures the flow of fluids through each of the supply lines. The rate at which the process and carrier fluids including, for example, silane ($SiH_4$), nitrous oxide ($N_2O$), argon (Ar) nitrogen ($N_2$), and/or other dopant or reactant sources, are supplied to processing chamber 16 is also controlled by temperature-based liquid or gas mass flow controllers (MFCs) (not shown) and/or by valves (not shown). In alternative embodiments, the rate at which the process and carrier fluids are supplied to the processing chamber 16 may be controlled by a pressure-based, fixed or variable aperture. Were toxic fluids, such as, ozone ($O_3$), or halogenated gas, used in a process, the several shut-off valves may be positioned on each gas supply line in conventional configurations. Gas supply panel 104 has a mixing system that receives the deposition process and carrier fluids from the sources 106 for mixing and sending to a throughway 50a in a gas-feed cover plate 50 via supply lines 108. In the specific embodiment, the mixing system, the input manifold to the mixing system, and the output manifold from the mixing system to the throughway 50a may be made of nickel or of a material such as alumina plated with nickel.

In operation, the pedestal 86 places the substrate 90 in the process zone 92 and process fluids are received from the source 106 into the throughway 50a, through the gas-feed cover plate 50, the baffle plate 52, and the showerhead 54 to enter the processing zone 92. The process fluids flow radially outward across the edge of substrate 90 reacting with the exposed surface thereof to form a desired film. Thereafter, the fluid flow is deflected upwardly over the ring 96 and into pumping channel 70 via the choke aperture 98. Upon entering pumping channel 70, the exhaust gas is routed around the perimeter of the processing chamber 16, to be evacuated by the vacuum pump 82.

Referring to FIGS. 1, 2 and 3 to monitor the effects that a process has on the substrate 90 and/or a film formed thereon, characteristics of the substrate 90, or film being formed thereon, are measured as a function of the spectral emission of the plasma present. To that end, spectral bands are identified that contain information concerning certain characteristics of the film. This is empirically determined by analyzing spectra of films having different thicknesses. In one example, multiple substrates, each of which is approximately 300 mm in diameter, are analyzed during deposition of a silicon containing film thereon. Specifically, in this example the RF power supply system 30 supplied a voltage in the range of 283 to 437 Watts and the pedestal 86 placed the substrate 90 a predetermined distance from the showerhead 54 in the range of 475 to 550 mils. The chamber pressure was established by the vacuum system 28 to be in the range of 2.43 to 2.97 milliTorr. The gas delivery system 26 supplied silane, $SiH_4$, into the processing chamber 16 from one of the sources 106 at a rate in the range of 247–260 sccm. A flow of nitrous oxide, $N_2O$ was introduced from one of the sources 106 at a rate in the range of 3,325 to 3,850 sccm. Specifically, the spectral response from the plasma 110 is analyzed for a set of substrates having a film deposited thereon at a baseline deposition rate, i.e., with the aforementioned parameters being set at the center-point of the ranges provided. From this center-point, or baseline, spectra are observed. The spectra are sensed for substrates having films deposited with the aforementioned parameters being varied from the center-point, thereby altering the deposition rates, from the baseline deposition rate, at which the films are being deposited. These spectra are compared to the baseline spectra. Specifically, the ranges of wavelength that demonstrate an intensity change, with respect to the intensity of the baseline spectra, are identified as containing information corresponding to the film characteristic of interest: in this example the deposition rate of a film being deposited on the substrate 90.

With the aforementioned process parameters a range of wavelengths, from 200 to 900 nm, is sensed employing a multi-channel CCD sensor assembly. In the present example, a CCD sensor has an array of 2048 pixels, each of which is associated with a differing band of wavelengths of spectral energy providing a spectral resolution of 0.32 nm per pixel. In each pixel, the time-averaged intensity of the wavelengths associated therewith is obtained. Specifically for each pixel of the CCD sensor, the spectral energy is sensed six times a second, i.e., once every 163 ms referred to as integrated data. An average of the integrated data is obtained providing a data point. Sixty data points are obtained, referred to as preliminary intensity data. After obtaining the preliminary intensity data, the plasma 110 is extinguished and measurements are taken with the CCD sensor, referred to as background radiation measurements. The background measurements are taken for approximately ten seconds. After the background radiation measurements have been taken the information contained therein is subtracted from the preliminary intensity data to provide corrected intensity data. The average of the corrected intensity data is obtained, thereby providing the time-averaged intensity referred to above.

Figure 4:
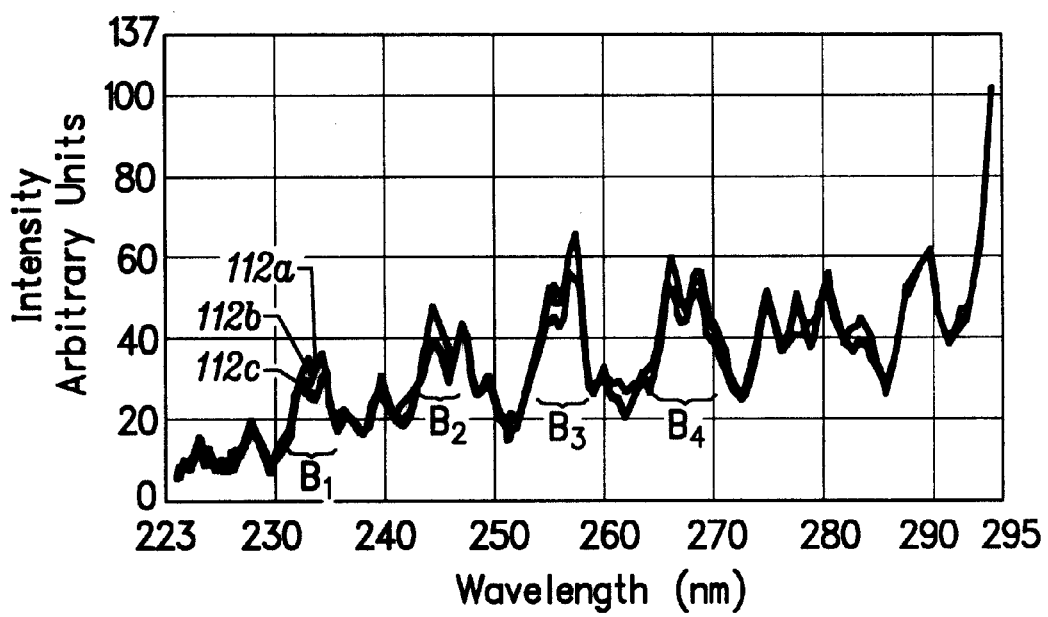
FIG. 4 is a graphical representation of intensity levels vs. bandwidth showing intensity variations in a first range of wavelengths of the emission spectra from the plasma generated in the processing chamber, shown above in FIGS. 1–3, that correspond to variations in film characteristics in accordance with the present invention.
Figure 5:
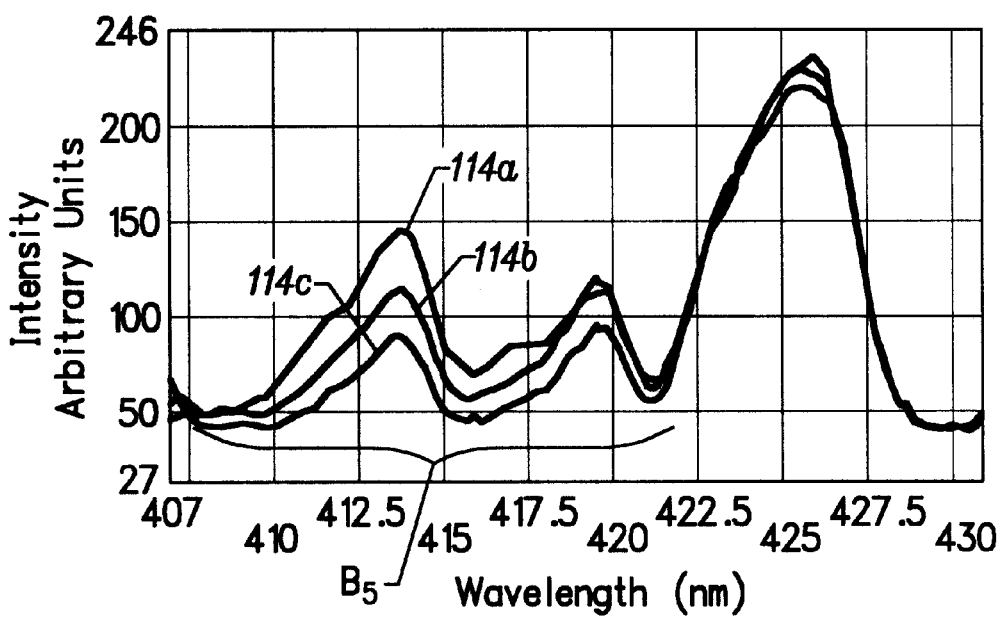
FIG. 5 is a graphical representation of intensity levels vs. bandwidth showing intensity variations in a second range of wavelengths of the emission spectra from the plasma generated in the processing chamber, shown above in FIGS. 1–3, which correspond to variations in film characteristics in accordance with the present invention.

Referring to FIGS. 4 and 5, based upon the curves 112a, 112b and 112c, it was found that the wavelength λ in the range of 230 to 275 nm contained information corresponding to certain film characteristics, such as deposition rate. Specifically, curve 112b represents baseline spectra that correspond to the emission spectra of the plasma 110, shown in FIG. 1, for substrates having films being deposited thereon at the baseline deposition rate. The baseline spectra 112b is compared with the spectra associated with substrates having films being deposited thereon at a deposition rate that differs from the baseline deposition rate, i.e., spectra 112a and 112c. It is seen from this comparison that four spectral bands, shown as $B_1$, $B_2$, $B_3$ and $B_4$, demonstrate variations in intensity that correspond to different deposition rates. These bands are considered indicative of the deposition rate characteristics of the film, because of the deviation of the spectra 112a and 112c in the bands $B_1$, $B_2$, $B_3$ and $B_4$ is greatest, compared to other bands of the spectra 112a, 112b and 112c.

However, it was found that two bands of wavelengths in the range of 400 to 430 nm contained information that corresponded very closely to film deposition rate, shown by curves 114a, 114b and 114c. Specifically, variations of intensity between emissions corresponding to different deposition rates was found in a band of wavelengths, $B_5$, in the range of 408 to 421 nm. Thus, the band of wavelengths, $B_5$, is highly indicative of variations in the film deposition rate, referred to as correlated spectral bands. By sensing the correlated spectral bands, monitoring of the change in various film characteristics could be achieved.

In the most direct manner, the film characteristics may be monitored by creating a look-up table in memory 38, shown in FIG. 2, in which information concerning wavelength intensity and the desired film characteristic, in this case film thickness, is stored. Specifically, the look up table would associate film thickness with both a flange of wavelengths and intensity levels that would be determined empirically, and stored in the memory 38.

Figure 6:
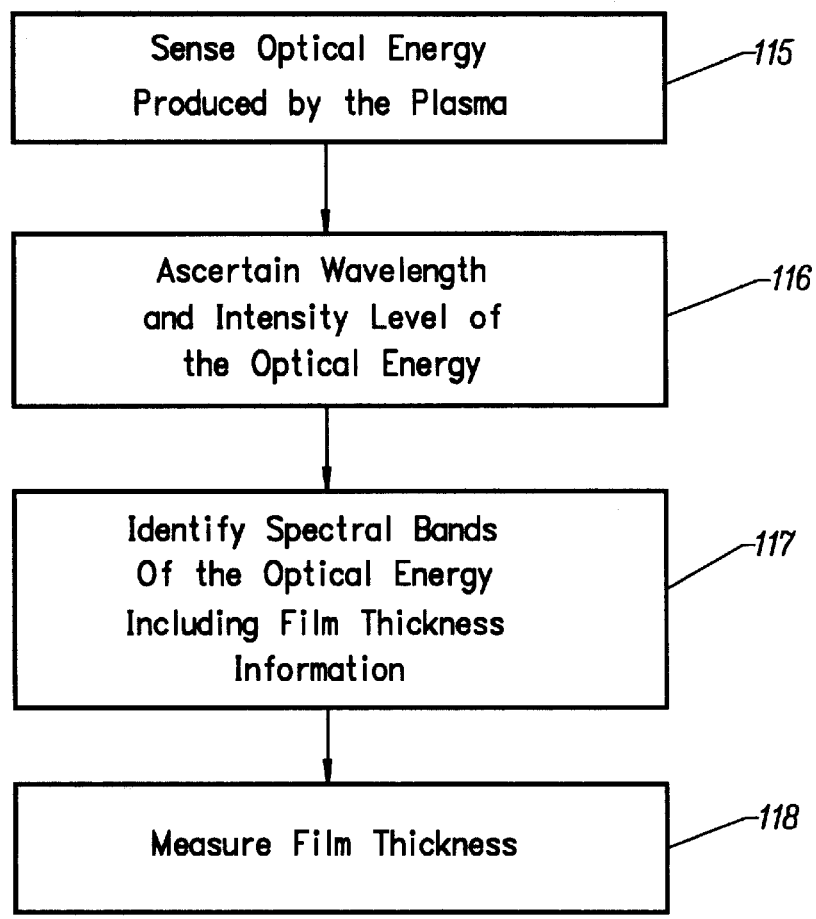
FIG. 6 is a flow chart showing the steps of the method for measuring film characteristics as a function of the wavelength and intensity of optical energy, in accordance with the present invention.

Referring to FIGS. 1, 2 and 6, during operation, optical energy produced by the plasma 110 would be sensed by the spectrum analyzer 22 at step 115 and a signal would be generated in response thereto. The processors 36 would operate on the signal to quantize, e.g. digitize the same and ascertain the wavelengths and intensity levels of the optical energy sensed by the spectrum analyzer 22 at step 116. At step 117, the processor 36 would identify spectral bands from the wavelengths that contain information corresponding to film thickness. To that end, the processor 36 would operate on data entries in the memory 38 to find a data entry having wavelength information that matches the wavelength sensed by the spectrum analyzer 22 defining matched data. Thereafter, the processor 36 would find among the matched data, intensity information that matched the intensity of the optical energy sensed by the spectrometer 22. This may be achieved by finding an exact correspondence or through an interpolative process to determine the data entry that is the closest match to the wavelength and intensity of the sensed optical energy. Once the appropriate data entry is ascertained, the film thickness associated with the appropriated data entry becomes the measure of the film thickness at step 118. As this is a continuing process, the deposition rate may be determined from a plurality of film thickness measurements during a unit of time. From the film thickness information, the stress of the film may be determined using known techniques.

Referring again to FIG. 1, several events are likely to occur that have deleterious effects on the accuracy of the measurements obtained with the processing system 12. These events include, clouding of the chamber window 20 due to particulates or non-volatile materials produced as by-products of the plasma deposition process. In addition, pre-amp drift in the spectrum analyzer 22 or degradation of the fiber optic cable 24 might occur that would also reduce the accuracy of the measurements. Thus, to ensure accurate measurements, periodic calibration of the processing system 12 would be undertaken using standard techniques.

A typical calibration technique requires illuminating the spectrometer optics entrance aperture that consists of the chamber window 20 and the entrance aperture of the fiber optic cable 24 with a broadband light source of known luminosity, such as a sodium lamp inserted into the processing chamber 16. Alternatively, a nitrogen plasma may be struck inside the processing chamber 16 to function as the broadband light source. Regardless of the light source employed, determining when to calibrate the processing system 12 may require closely monitoring chamber, process, optics, and spectrometer conditions to determine when a recalibration is necessary and/or insert a calibration step between each process run. This would reduce throughput by increasing processing time.

To abrogate the need to calibrate the processing system 12, an additional embodiment of the present invention includes identifying spectral bands of the emission spectrum of the plasma 110 having an intensity that is relatively insensitive to the film characteristics. To that end, spectral bands containing information that is substantially independent of the film characteristics are identified, referred to as disjunctive spectral bands.

From this information the characteristics of the film on the substrate 90 is determined as follows:

$$\text{Characteristic} \sim a_1 R_1 + \text{constant} \tag{1}$$

where Ri represents ratios of correlated spectral bands to disjunctive spectral bands. The constant "a" represents coefficients derived by a statistical mapping model of the characteristics value versus the ratio index. Specifically, a plurality of values of a characteristic of interest is mapped along one axis. The corresponding ratio $R_j$ that corresponds to each of the plurality of values is mapped along an orthogonal axis. A curve is fitted to the graph that is the closest fit to a linear function. This curve is represented by the coefficient "a". Each ratio has the form:

$$R_i = \left( \frac{\sum_j I_j^{correlated}}{I_i^{disjunctive}} \right) \tag{2}$$

for referencing multiple characteristics to a single correlated spectral band. For referencing a single disjunctive spectral band to a single characteristic the ratio is as follows:

$$R_i = \left( \frac{I_i^{correlated}}{I_i^{disjunctive}} \right)^k \tag{3}$$

where k=±1. Using a model based on spectral ratios rather than the absolute intensities of spectral bands abrogates the need for an absolute calibration of the PECVD system 12, because relative intensities of the plasma spectra are sensed.

Figure 7:
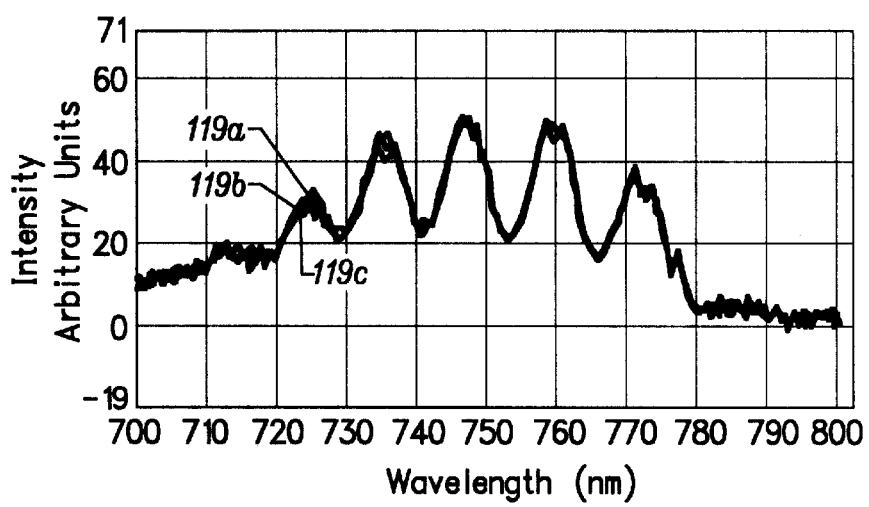
FIG. 7 is a graphical representation of intensity levels vs. bandwidth showing intensity variations in a third range of wavelengths of the emission spectra from the plasma generated in the processing chamber, shown above in FIGS. 1–3, that are independent of variations in film characteristics in accordance with the present invention.

In the present example, disjunctive spectral bands are identified as lying in the range of 700 to 800 nm, shown by curves 119a, 119b and 119c in FIG. 7. The curves 119a, 119b and 119c are considered disjunctive, because there is little deviation by the spectra represented by curves 119a and 119c, from the baseline spectrum represented by curve 119b. After obtaining the information in both the correlated spectral bands and the disjunctive spectral bands, i.e., the correlated information and disjunctive information, respectively, the information is quantized, e.g., digitized. In one example, the quantification is obtained as a function of the number of photons (counts) sensed by the appropriate pixels of the CCD sensor 18a. The measurements obtained are indicated below in the Table.

TABLE

| Substrate Number | number of counts for $\lambda_1$ =410– 416 nm | number of counts for $\lambda_2$ =730– 780 nm | ratio $\lambda_2/\lambda_1$ | film thickness Å/min | Stress dynes/cm$^2$ |
|---|---|---|---|---|---|
| 1 | 1186.659 | 6041.242 | 5.0910 | 10087 | −1.41E + 09 |
| 2 | 1317.858 | 5942.300 | 4.5091 | 11626 | −1.03E + 09 |
| 3 | 1023.549 | 5248.461 | 5.1277 | 9338 | −1.27E + 09 |
| 4 | 1179.602 | 6138.719 | 5.2041 | 10054 | −1.44E + 09 |
| 5 | 1172.053 | 6110.246 | 5.2133 | 10069 | −1.42E + 09 |
| 6 | 1141.079 | 5826.429 | 5.1061 | 10257 | −1.39E + 09 |
| 7 | 1366.681 | 6444.437 | 4.7154 | 11450 | −1.08E + 09 |
| 8 | 1283.168 | 6417.424 | 5.0012 | 11083 | −1.54E + 09 |
| 9 | 1313.715 | 6576.993 | 5.0064 | 11009 | −1.57E + 09 |
| 10 | 1127.904 | 6538.636 | 5.7972 | 8591 | −1.73E + 09 |
| 11 | 997.285 | 5556.954 | 5.5721 | 8602 | −1.78E + 09 |
| 12 | 1291.051 | 5538.737 | 4.2901 | 11544 | −7.93E + 08 |
| 13 | 1163.242 | 6124.791 | 5.2653 | 10033 | −1.43E + 09 |
| 14 | 1101.174 | 5290.505 | 4.8044 | 10390 | −1.13E + 09 |
| 15 | 1256.497 | 5367.168 | 4.2715 | 11428 | −7.74E + 08 |
| 16 | 1094.177 | 6661.333 | 6.0880 | 7866 | −1.96E + 09 |
| 17 | 966.626 | 5589.949 | 5.7829 | 8298 | −1.91E + 09 |
| 18 | 1263.14 | 5813.183 | 4.6022 | 11280 | −1.28E + 09 |
| 19 | 890.474 | 5623.087 | 6.3147 | 7669 | −1.95E + 09 |
| 20 | 1183.883 | 5979.457 | 5.0507 | 10437 | −1.19E + 09 |
| 21 | 928.551 | 5892.844 | 6.3463 | 7845 | −1.92E + 09 |
| 22 | 1159.206 | 6128.114 | 5.2865 | 10040 | −1.43E + 09 |
| 23 | 1202.617 | 6212.342 | 5.1657 | 10173 | −1.37E + 09 |
| 24 | 1503.508 | 6135.152 | 4.0806 | 12825 | −7.37E + 08 |
| 25 | 1194.844 | 5835.934 | 4.8843 | 10534 | −9.53E + 08 |
| 26 | 1411.519 | 6621.301 | 4.6909 | 11767 | −8.60E + 08 |
| 27 | 1025.784 | 5795.464 | 5.6498 | 8562 | −1.88E + 09 |
| 28 | 1319.994 | 5572.673 | 4.2217 | 11863 | −5.61E + 08 |
| 29 | 1078.232 | 5730.516 | 5.3147 | 9777 | −1.59E + 09 |
| 30 | 1392.357 | 5707.351 | 4.0991 | 12214 | −9.45E + 08 |
| 31 | 946.928 | 5767.088 | 6.0903 | 7270 | −2.18E + 09 |
| 32 | 1362.005 | 6887.343 | 5.0568 | 11310 | −1.35E + 09 |
| 34 | 1234.571 | 6280.458 | 5.0872 | 10406 | −1.21E + 09 |
| 35 | 1041.915 | 5484.732 | 5.2641 | 9229 | −1.32E + 09 |
| 36 | 1038.364 | 6230.018 | 5.9998 | 8318 | −1.85E + 09 |
| 37 | 1229.706 | 7053.782 | 5.7362 | 9469 | −1.69E + 09 |
| 38 | 1132.681 | 6325.358 | 5.5844 | 9514 | −1.77E + 09 |
| 39 | 1323.448 | 6288.111 | 4.7513 | 11401 | −1.06E + 09 |
| 40 | 1075.574 | 6234.882 | 5.7968 | 8768 | −1.65E + 09 |
| 41 | 1009.983 | 6302.873 | 6.2406 | 7676 | −2.07E + 09 |
| 42 | 1216.913 | 5655.209 | 4.6472 | 11233 | −1.16E + 09 |
| 43 | 1466.267 | 5993.89 | 4.0879 | 12685 | −7.18E + 08 |
| 44 | 973.928 | 5404.775 | 5.5495 | 8843 | −1.56E + 09 |
| 45 | 1054.928 | 6414.281 | 6.0803 | 7952 | −2.01E + 09 |
| 46 | 1158.665 | 6139.201 | 5.2985 | 10023 | −1.45E + 09 |
| 47 | 1110.049 | 5905.991 | 5.3205 | 9682 | −1.64E + 09 |

Figure 8:
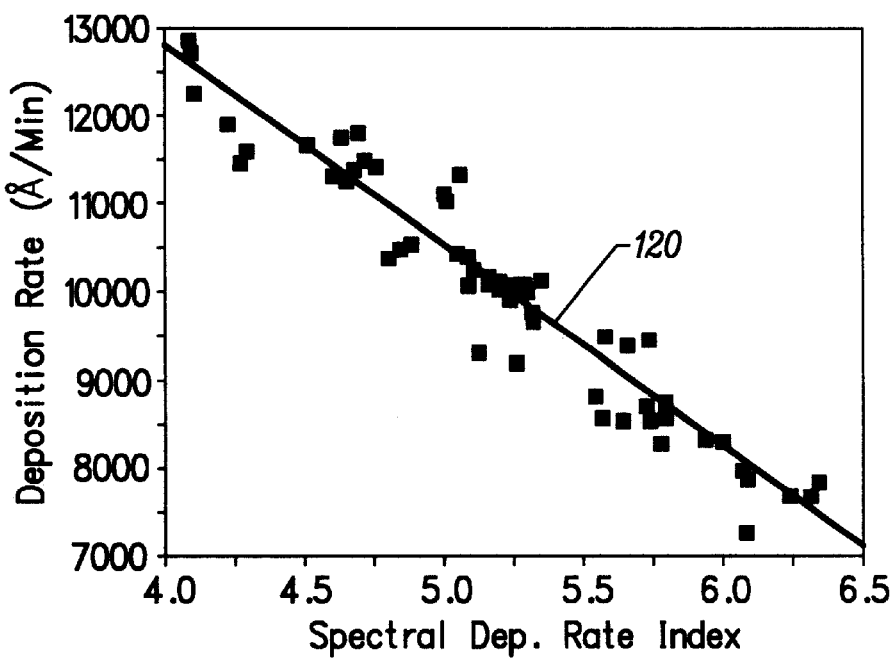
FIG. 8 is a is a graphical representation of deposition rates vs. ratio of correlated spectral bands in the range 410 nm to 416 nm to disjunctive spectral bands in the range of 730 nm to 790 nm for 101 substrates generated by the plasma in the processing chamber, shown above in FIGS. 1–3, in accordance with the present invention.

The ratio of the quantized correlated information to the quantized disjunctive information is obtained for each substrate as indicated above in the column identified as ratio, and the characteristics of the film are determined as a function of the same. This is indicated above in the columns of the Table and graphically demonstrated in FIGS. 8 and 9.

Specifically, the ratio shown above in the Table represents the best-fit data, i.e., the data with the closest correlation to the measured film characteristics, from several ratios that were examined. As shown from the slope of line 120 in FIG. 8, employing a ratio of the 730–780 nm band to the 410–416 nm, a high correlation was achieved having an $R^2$ value of 0.90. It was also found that the ratio of the 730–780 nm band to the 416–421 nm band also successfully correlated with the film thickness. However, the correlation was less than that obtained from the ratio of the 730–780 nm band to the 410–416 nm. The correlation of the ratio of the 730–780 nm band to the 416–421 nm band achieved an $R^2$ value of approximately 0.80. Thus, in the present example, it was desired to determine film thickness and, therefore, deposition rate, as a function of the ratio of the 730–780 nm band to the 410–416 nm. In this fashion, information concerning the deposition rate of the film may be obtained relatively independent of degradation in the system optics and chamber conditions. As mentioned above, information concerning deposition rate facilitates determination of various film characteristics, such as film stress.

Figure 9:
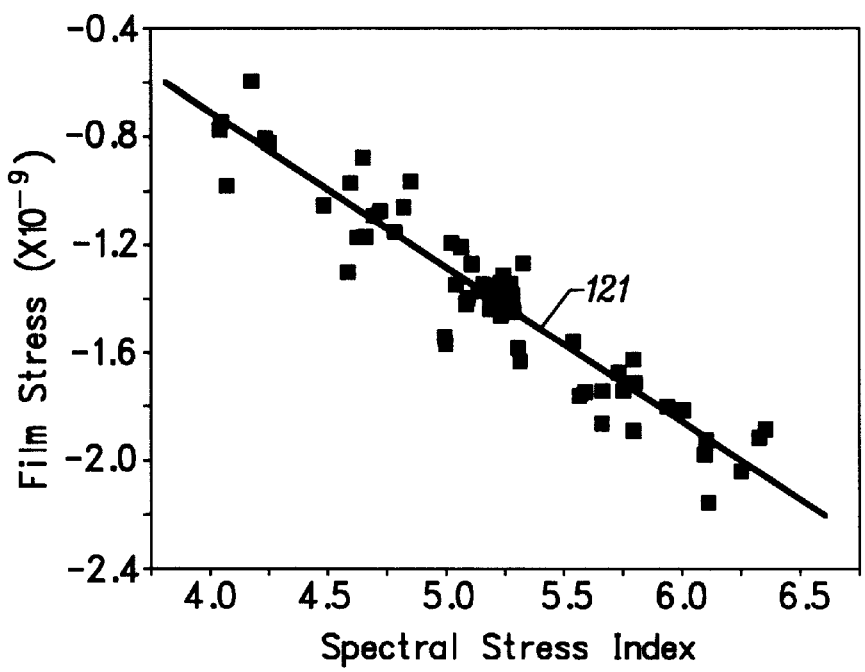
FIG. 9 is a graphical representation of film stress vs. ratio of correlated spectral bands in the range 410 nm to 416 nm to disjunctive spectral bands in the range of 730 nm to 790 nm for 101 substrates generated by the plasma in the processing chamber, shown above in FIGS. 1–3, in accordance with the present invention.

Referring to the slope of the line 121 in FIG. 9, it is seen that a high correlation was achieved having an $R^2$ value of 0.93 employing a ratio of the 730–780 nm band to the 410–416 nm band. The ratio of the 730–780 nm band to the 416–421 nm band also successfully correlated with the film stress, but with an R2 value that was about 0.10 less. It should be noted that the correlation between the results obtained by the present example and the film characteristics being measured may be improved employing a greater number of spectral bands. From the results shown above in FIGS. 4–6, at least eight additional correlative spectral bands may be identified. Obtaining additional ratios of these additional spectral bands with the appropriate disjunctive bands may greatly improve the correlation between the ratios obtained and the film characteristics being measured. As a result, equation (1) would be expressed as follows:

$$\text{Characteristic} \sim a_1R_1 + a_2R_2 + a_nR_n + \text{constant} \quad (4)$$

where n=8 in this example.

Figure 10:
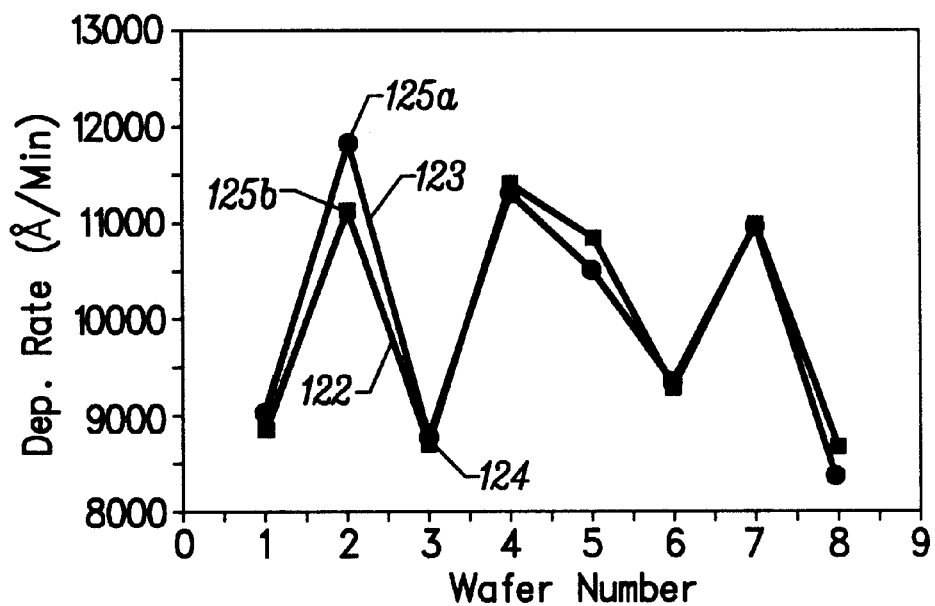
FIG. 10 is a graphical representation comparing values sensed using the present invention and measured values of the deposition rate for eight of the 101 substrates discussed above with respect to FIGS. 8 and 9, in accordance with the present invention.

Referring to FIG. 10, it is seen that ratios of correlated and disjunctive spectral bands provide accurate measurements of the film characteristics by demonstrating a comparison between the values of the film deposition rate obtained using the present invention, referred to as sensed values, and values of the film deposition rate using standard measured techniques, referred to as measured values. Specifically, the curve 122 represents sensed values of deposition rates for eight substrates, employing the present invention. The curve 123 represents the measured values of deposition rates for the same eight substrates. It is seen that the measured value for the third substrate, shown at point 124, matches the sensed value almost exactly. The worst match is found for the second substrate, shown as points 125a and 125b. The point 125a represents the measured value of the deposition rate for substrate number two and it differs from the sensed value of the deposition rate, shown as point 125b, by approximately 500 Å per minute. Nonetheless, the deviation between the sensed and measured values of the deposition rate of these eight substrates averaged less than 2%. Thus, the aforementioned ratios of the spectral bands provided information that is highly indicative of the deposition rate of a film and, therefore, the film thickness.

Figure 11:
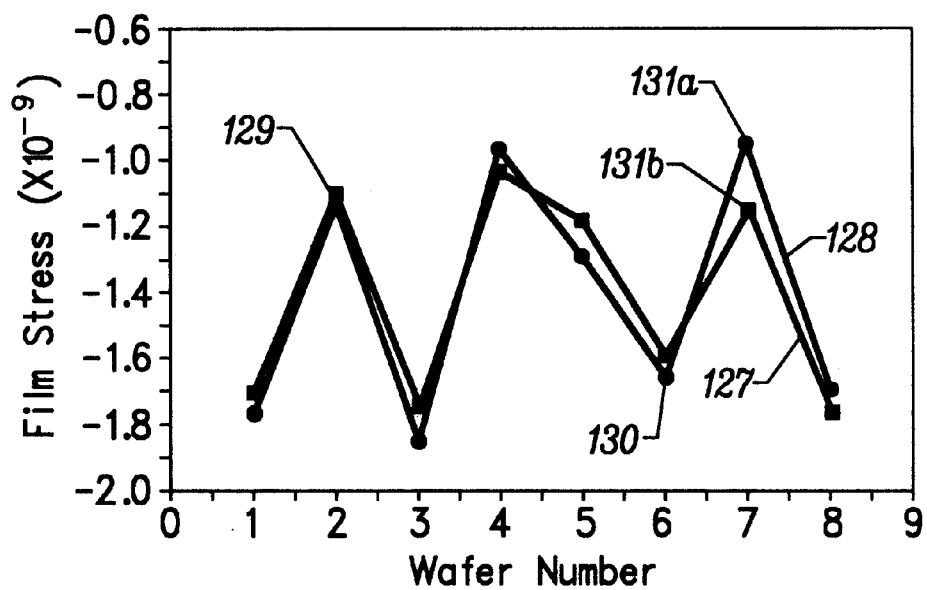
FIG. 11 is a graphical representation comparing sensed values using the present invention and measured values of the film stress for eight of the 101 substrates discussed above with respect to FIGS. 8 and 9, in accordance with the present invention.

FIG. 11 demonstrates that the aforementioned ratios provide accurate measurements of the film characteristics by demonstrating that the deviation between sensed and measured values of the film stress. Specifically, the curve 127 represents a sensed value of the deposition rate for eight substrates, employing the present invention. The curve 128 represents the measured value of the deposition rate for the same eight substrates. It is seen that the measured value of the deposition rate for the second and sixth substrates, shown at points 129 and 130, respectively, matches the sensed values of the deposition rates almost exactly. The worst match is found for the seventh substrate. The point 131a represents the measured value of the deposition rate for substrate number nine and it differs from the sensed value of the deposition rate, shown as point 131 b by approximately $2.00 \times 10^8$ dynes/cm². Nonetheless, the deviation between the sensed and measured values of the film stress averaged about 7.5%.

Figure 12:
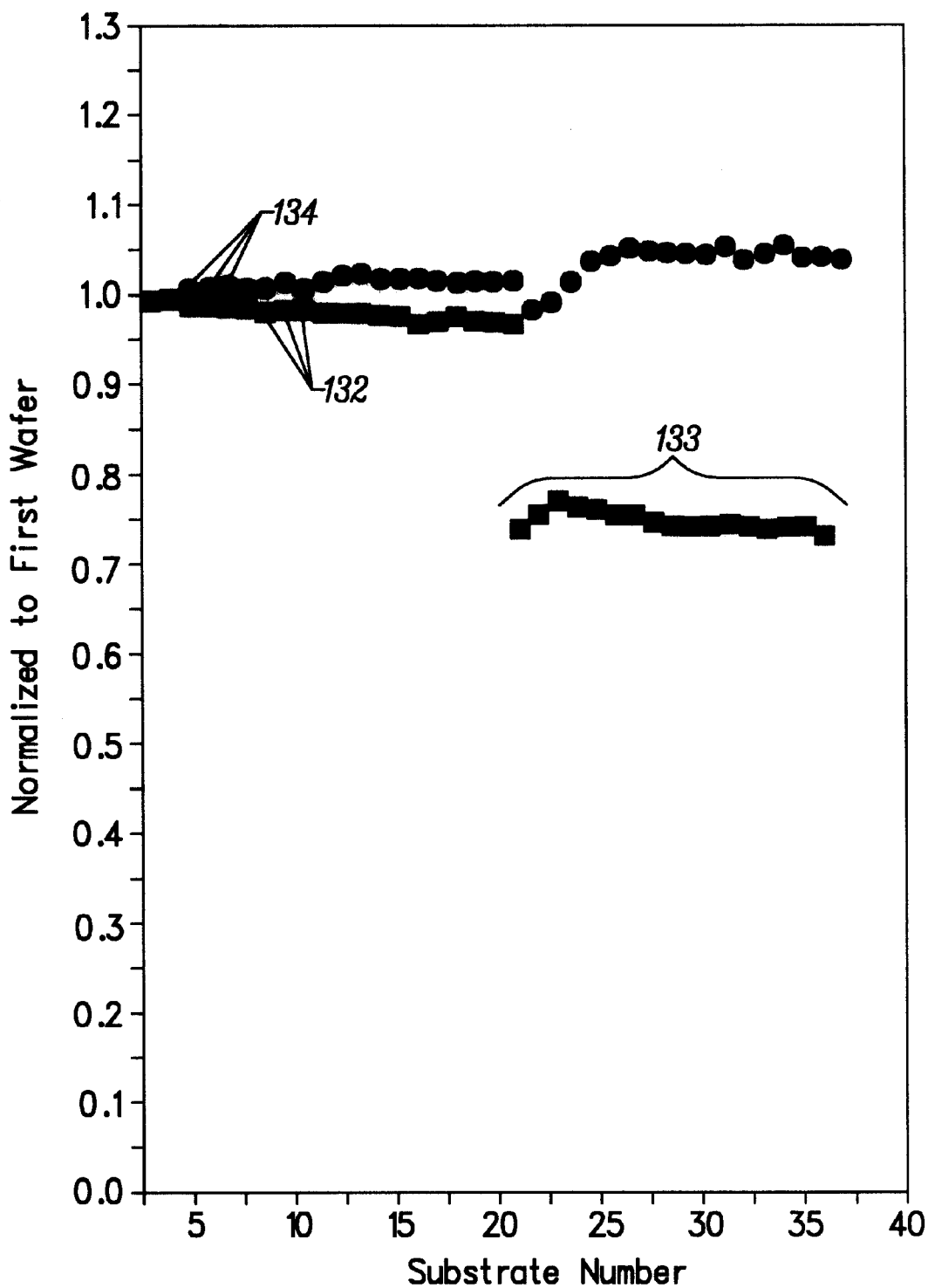
FIG. 12 is a graphical representation showing the intensity of optical energy detected for the correlated spectral bands in the range of 410 nm to 416 nm compared to a graphical representation of the ratio of spectral intensity of correlated spectral bands in the range 410 nm to 416 nm to disjunctive spectral bands in the range of 730 nm to 790 nm for 101 substrates.
Figure 13:
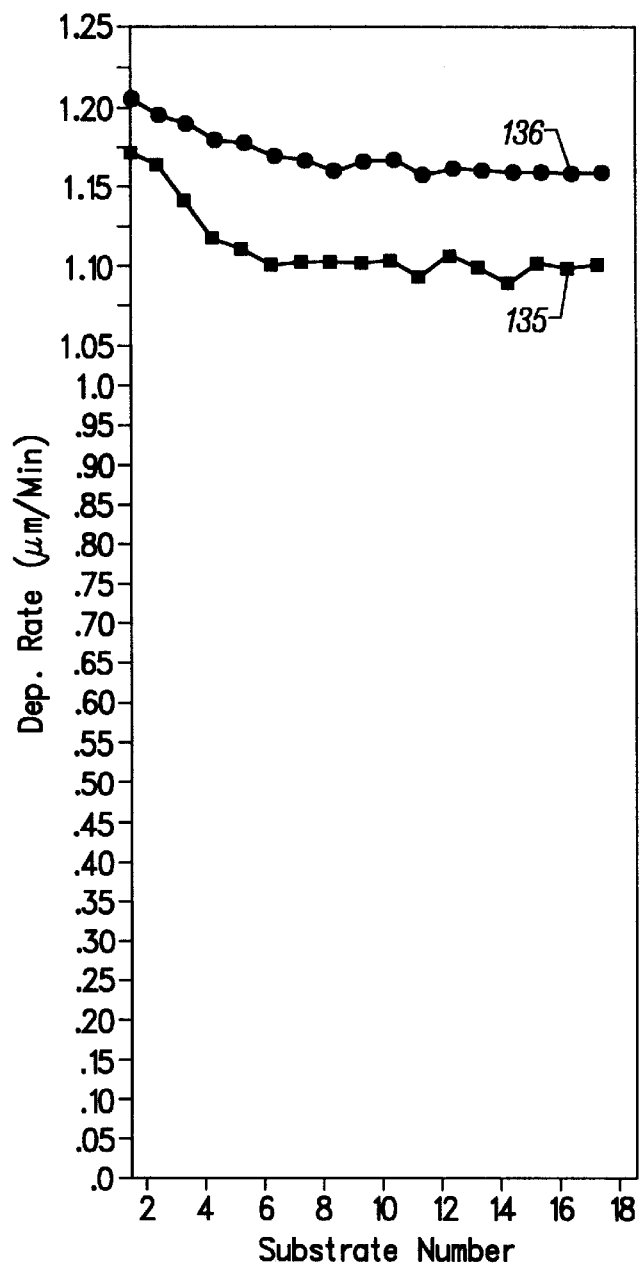
FIG. 13 is a graphical representation comparing sensed values using the present invention and measured values of the deposition rate for seventeen of the 101 substrates discussed above with respect to FIG. 12, in accordance with the present invention.
Figure 14:
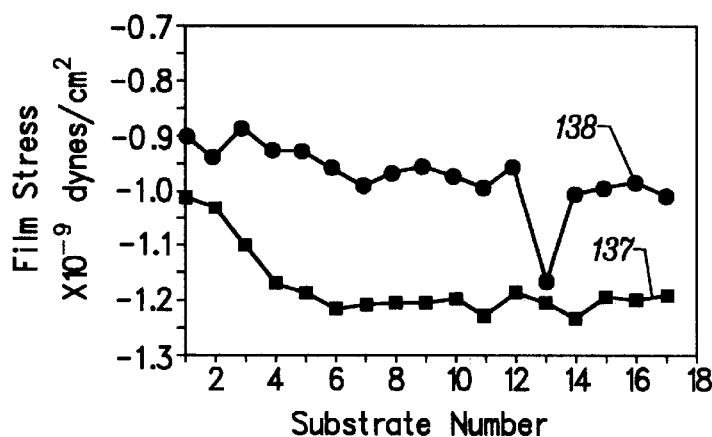
FIG. 14 is a graphical representation comparing sensed values using the present invention and measured values of the film stress for seventeen of the substrates discussed above with respect to FIGS. 12 and 13, in accordance with the present invention.

Referring to FIGS. 12, 13 and 14, the robustness of measuring film characteristics as a function of the ratio of correlated and disjunctive bands is demonstrated. Specifically, FIG. 12 shows a plurality of normalized intensity measurements, shown as points 132 were made detecting optical energy in the correlated spectral band of 410 nm to 416 nm. Referring to region 133 of the graph, a 20% reduction in intensity is measured for seventeen substrates, i.e. substrates 20 through 37. However, it is shown that the intensity measured for substrates 20 through 37, employing the aforementioned ratios, shown by points 134, varied less than 5%. Thus, accurate measurements of the film characteristics may be obtained even though the processing system drifts out of calibration.

FIGS. 13 and 14 demonstrate that employing the ratio of correlated and disjunctive bands maintains the deviation between the sensed and measured film characteristics within acceptable ranges independent of intensity variations due to deleterious effects of semiconductor processes. The curve 135 represents a sensed deposition rate, for seventeen substrates mentioned above with respect to FIG. 12, and the curve 136 represents the measured deposition rate for the same seventeen. Comparing curves 135 and 136 it is seen that the deviation between the sensed and measured values of the deposition rate of these seventeen substrates was less than 4.5%.

The deviation between the sensed and measured values of the film stress for the same seventeen substrates mentioned above with respect to FIG. 13 is demonstrated by comparing curve 137 of FIG. 14, which represents the sensed values of the film stress, with curve 138, which represents the measured values of the film stress. Specifically, the deviation between the sensed and measured values of the film stress for the same eighteen substrates was less than 15%. Thus, it can be deduced that the deleterious effects, in this case, clouding of the window 20, shown in FIG. 1, by contaminants, has little consequence for film characteristic measurements employing the ratios of correlated to disjunctive spectral bands.

As discussed above with respect to FIG. 2, the processor 36 controls the operation of the PECVD system. This is achieved by having the processor 36 operate on system control software that is stored in a memory 38. The computer program includes sets of instructions that dictate the timing, mixture of fluids, chamber pressure, chamber temperature, RF power levels, and other parameters of a particular process, discussed more fully below. The memory 38 may be any kind of memory, such as a hard disk drive, floppy disk drive, random access memory, read-only-memory, card rack or any combination thereof. The processor 36 may contain a single-board computer (SBC), analog and digital input/output boards, interface boards and stepper motor controller boards that may conform to the Versa Modular European (VME) standard that defines board, card cage, and connector dimensions and types. The VME standard also defines the bus structure as having a 16-bit data bus and a 24-bit address bus.

Figure 15:
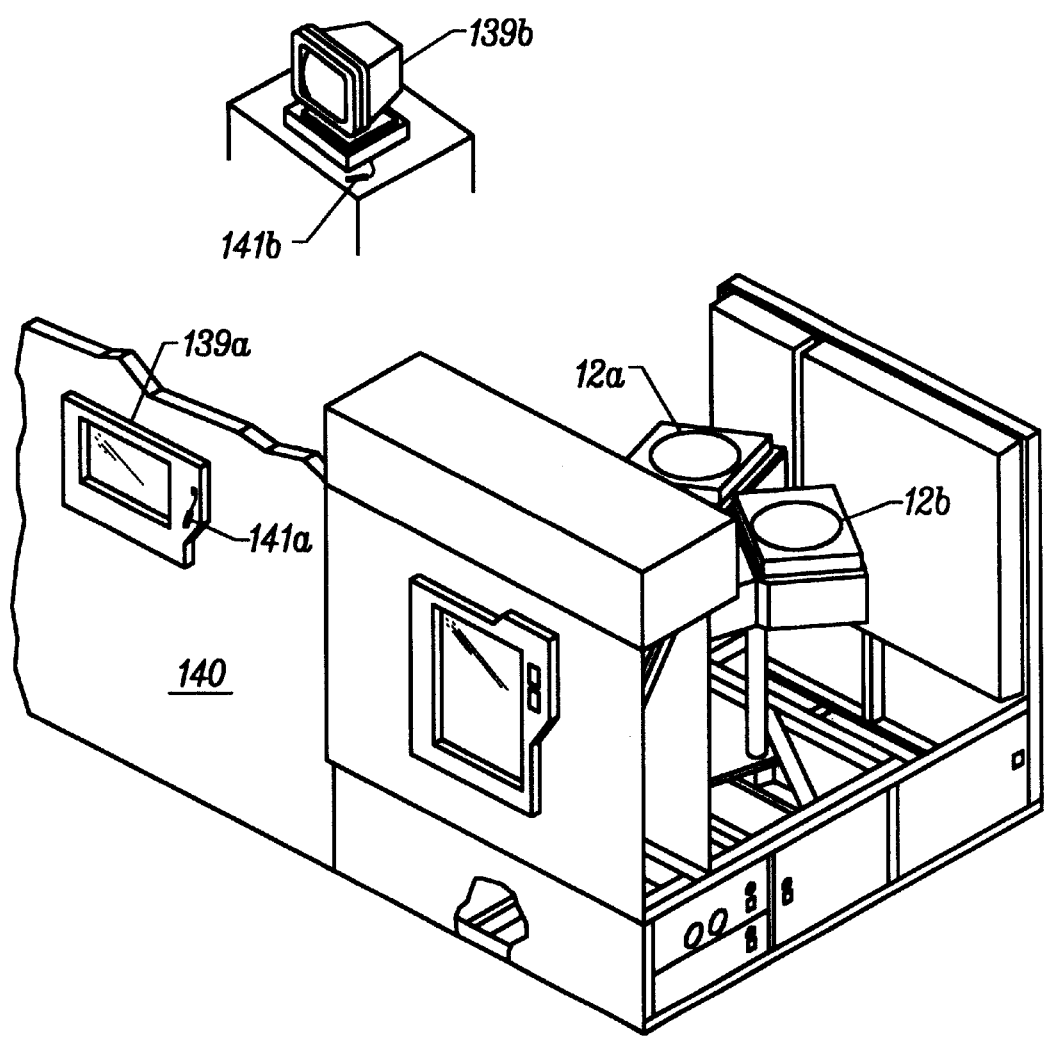
FIG. 15 is a perspective view of a processing environment in which the processing chambers, shown above in FIGS. 1–3, may be employed.

Referring to both FIGS. 2 and 15, the interface between a user and the processor 36 may be via a visual display. To that end, two monitors 139a and 139b may be employed. One monitor 139a may be mounted in a clean room wall 140 having one or more PECVD systems 12a and 12b. The remaining monitor 139b may be mounted behind the wall 140 for service personnel. The monitors 139a and 139b may simultaneously display the same information. Communication with the processor 36 may be achieved with a light pen associated with each of the monitors 139a and 139b. For example, light pen 141a facilitates communication with the processor 36 through monitor 139a, and light pen 141b facilitates communication with the processor 36 through monitor 139b. A light sensor in the tip of the light pens 141a and 141b detects light emitted by CRT display in response to a user pointing the same to an area of the display screen. The touched area changes color, or a new menu or screen is displayed, confirming communication between the light pens 141a and 141b and the display screen. Other devices, such as a keyboard, mouse, or other pointing or communication device, may be used instead of or in addition to the light pens 141a and 141b to allow the user to communicate with the processor 36.

As discussed above, the computer program includes sets of instructions that dictate the timing, mixture of fluids, chamber pressure, chamber temperature, RF power levels, and other parameters of a particular process, as well as analyzing the information obtained by the spectrum analyzer 22 discussed more fully below. The computer program code may be written in any conventional computer readable programming language: for example, 68000 assembly language, C, C++, Pascal, Fortran and the like. Suitable program code is entered into a single file, or multiple files, using a conventional text editor and stored or embodied in a computer-readable medium, such as a memory system of the computer. If the entered code text is in a high level language, the code is compiled, and the resultant compiler code is then linked with an object code of precompiled Windows® library routines. To execute the linked and, compiled object code the system user invokes the object code, causing the computer system to load the code in memory. The controller (not shown) then reads and executes the code to perform the tasks identified in the program.

Figure 16:
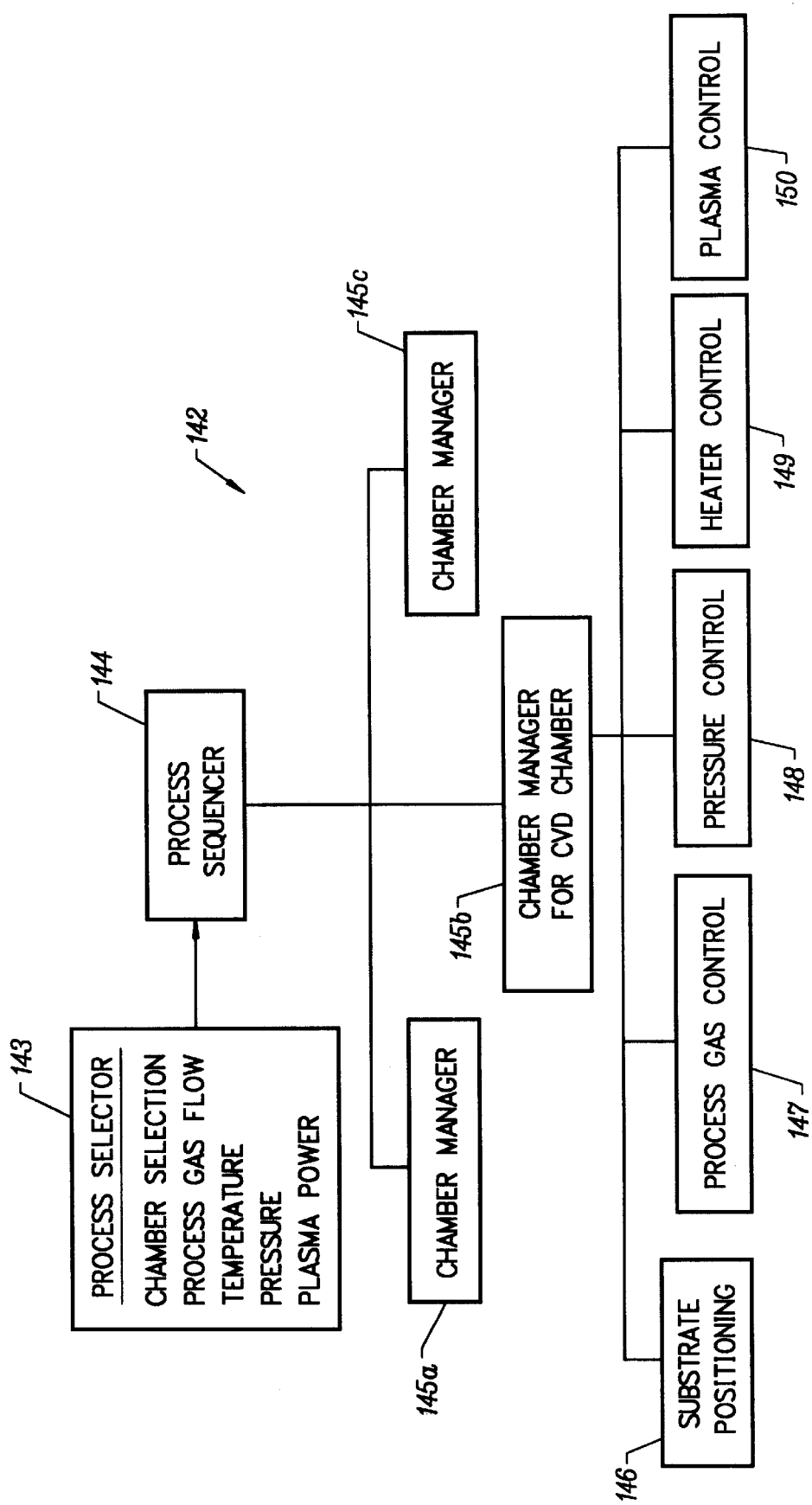
FIG. 16 is a block diagram showing the hierarchical control structure of system control software employed to control the processing system, shown above in FIG. 2.

Referring to FIG. 16, an illustrative block diagram of the hierarchical control structure of the system control software, computer program 142, according to a specific embodiment is shown. Using a light pen interface, a user enters a process set number and process chamber number into a process selector subroutine 143 in response to menus or screens displayed on the CRT monitor. The process sets, which are predetermined sets of process parameters necessary to carry out specified processes, are identified by predefined set numbers. Process selector subroutine 143 identifies (i) the desired process chamber, and (ii) the desired set of process parameters needed to operate the process chamber for performing the desired process. The process parameters for performing a specific process relate to process conditions such as, for example, process gas composition and flow rates, temperature, pressure, plasma conditions such as high- and low-frequency RF power levels and the high-frequency and low-frequency RF frequencies, (and in addition, microwave generator power levels for embodiments equipped with remote microwave plasma systems) cooling gas pressure, and chamber wall temperature. Process selector subroutine 143 controls what type of process (deposition, substrate cleaning, chamber cleaning, chamber gettering, reflowing) is performed at an appropriate time. In some embodiments, there may be more than one process selector subroutine 143.

A process sequencer subroutine 144 comprises program code for accepting the identified process chamber and set of process parameters from process selector subroutine 143, and for controlling operation of the various process chambers. Multiple users can enter process set numbers and process chamber numbers, or a single user can enter multiple process set numbers and process chamber numbers, so process sequencer subroutine 144 operates to schedule the selected processes in the desired sequence. Preferably, process sequencer subroutine 144 includes program code to perform the steps of (i) monitoring the operation of the process chambers to determine if the chambers are being used, (ii) determining what processes are being carried out in the processing chambers being used, and (iii) executing the desired process based on availability of a process chamber and the type of process to be carried out. Conventional methods of monitoring the processing chambers can be used, such as polling. When scheduling the process to be executed, process sequencer subroutine 144 may be designed to take into consideration the present condition of the processing chamber being used in comparison with the desired process conditions for a selected process, or the "age" of each particular user-entered request, or any other relevant factor a system programmer desires to include for determining scheduling priorities.

Once process sequencer subroutine 144 determines which processing chamber and process set combination is going to be executed next, the process sequencer subroutine 144 initiates execution of the process set by passing the particular process set parameters to a chamber manager subroutine 145a–c that controls multiple processing tasks according to the process set determined by process sequencer subroutine 144. For example, the chamber manager subroutine 145b comprises program code for controlling operations in processing Chamber 16. Chamber manager subroutine 145b also controls execution of various chamber component subroutines which control operation of the chamber components necessary to carry out the selected process set. Examples of chamber component subroutines cre substrate positioning subroutine 146, process gas control subroutine 147, pressure control subroutine 148, heater control subroutine 149, and plasma control subroutine 150. Depending on the specific configuration of the system chamber, some embodiments include all of the above subroutines, while other embodiments may include only some of the subroutines. Those having ordinary skill in the art would readily recognize that other chamber control subroutines can be included depending on what processes are to be performed in the processing chamber 16, shown in FIG. 2. In operation, chamber manager subroutine 145b selectively schedules or calls the process component subroutines in accordance with the particular process set being executed. Chamber manager subroutine 145b schedules the process component subroutines much like process sequencer subroutine 144 schedules which processing chamber 16 process set is to be executed next. Typically, chamber manager subroutine 145b includes steps of monitoring the various chamber components, determining which components need to be operated based on the process parameters for the process set to be executed, and initiating execution of a chamber component subroutine responsive to the monitoring and determining steps.

Referring to both FIGS. 3 and 16, the substrate positioning subroutine 146 comprises program code for controlling chamber components that are used to load the substrate onto pedestal 86 and, optionally, to lift the substrate 90 to a desired height in processing chamber 16 to control the spacing between the substrate 90 and showerhead 54. When a substrate 90 is loaded into processing chamber 16, pedestal 86 is lowered to receive the substrate 90 in substrate pocket 88, and then is raised to the desired height. In operation, substrate positioning subroutine 146 controls movement of pedestal 86 in response to process set parameters related to the support height that are transferred from chamber manager subroutine 145b.

Process gas control subroutine 147 has program code for controlling process gas composition and flow rates. Process gas control subroutine 147 controls the open/close position of the safety shut-off valves (not shown), and also ramps up/down the mass flow controllers (not shown) to obtain the desired gas flow rate. Process gas control subroutine 147 is invoked by the chamber manager subroutine 145b, as are all chamber component subroutines, and receives subroutine process parameters related to the desired gas flow rates from the chamber manager. Typically, process gas control subroutine 147 operates by opening the gas supply lines and repeatedly (i) reading the necessary mass flow controllers, (ii) comparing the readings to the desired flow rates received from chamber manager subroutine 145b, and (iii) adjusting the flow rates of the gas supply lines as necessary. Furthermore, process gas control subroutine 147 includes steps for monitoring the gas flow rates for unsafe rates, and activating the safety shut-off valves (not shown) when an unsafe condition is detected. Process gas control subroutine 147 also controls the gas composition and flow rates for clean gases as well as for deposition gases, depending on the desired process (clean or deposition or other) that is selected. Alternative embodiments could have more than one process gas control subroutine, each subroutine controlling a specific type of process or specific sets of gas lines.

In some processes, an inert gas such as nitrogen, $N_2$, or argon, Ar, is flowed into processing chamber 16 to stabilize the pressure in the chamber before reactive process gases are introduced. For these processes, process gas control subroutine 147 is programmed to include steps for flowing the inert gas into processing chamber 16 for an amount of time necessary to stabilize the pressure in the chamber, and then the steps described above would be carried out. Additionally, when a process gas is to be vaporized from a liquid precursor, for example $TiCl_4$, process gas control subroutine 147 would be written to include steps for bubbling a delivery gas, such as helium, through the liquid precursor in a bubbler assembly (not shown), or for introducing a carrier gas, such as helium, to a liquid injection system. When a bubbler is used for this type of process, process gas control subroutine 147 regulates the flow of the delivery gas, the pressure in the bubbler (not shown), and the bubbler temperature in order to obtain the desired process gas flow rates. As discussed above, the desired process gas flow rates are transferred to process gas control subroutine 147 as process parameters. Furthermore, process gas control subroutine 147 includes steps for obtaining the necessary delivery gas flow rate, bubbler pressure, and bubbler temperature for the desired process gas flow rate by accessing a stored table containing the necessary values for a given process gas flow rate. Once the necessary values are obtained, the delivery gas flow rate, bubbler pressure and bubbler temperature are monitored, compared to the necessary values and adjusted accordingly.

The pressure control subroutine 148 comprises program code for controlling the pressure in the processing chamber 16 by regulating the aperture size of the throttle valve 84 in the exhaust system of the chamber. The aperture size of the throttle valve 84 is set to control the chamber pressure at a desired level in relation to the total process gas flow, the size of the processing chamber 16, and the pumping set-point pressure for the exhaust system. When pressure control subroutine 148 is invoked, the desired or target pressure level is received as a parameter from chamber manager subroutine 145b. The pressure control subroutine 148 measures the pressure in the processing chamber 16 by reading one or more conventional pressure manometers connected to the chamber, compares the measure value(s) to the target pressure, obtains PID (proportional, integral and differential) values corresponding to the target pressure from a stored pressure table, and adjusts the throttle valve 84 according to the PID values obtained from the pressure table. Alternatively, pressure control subroutine 148 can be written to open or close the throttle valve 84 to a particular aperture size to regulate the pumping capacity in the processing chamber 16 to the desired level.

Heater control subroutine 149 comprises program code for controlling the temperature of a heater element 107 used to resistively heat pedestal 86 (and any substrate thereon). The heater control subroutine 149 is also invoked by the chamber manager subroutine 145b and receives a target, or set-point, temperature parameter. The heater control subroutine 149 measures the temperature by measuring voltage output of a thermocouple located in pedestal 86, comparing the measured temperature to the set-point temperature, and Increasing or decreasing current applied to the heating unit to obtain the set-point temperature. The temperature is obtained from the measured voltage by looking up the corresponding temperature in a stored conversion table, or by calculating the temperature using a fourth-order polynomial. When an embedded loop is used to heat pedestal 86, heater control subroutine 149 gradually controls a ramp up/down of current applied to the loop. Additionally, a built-in fail-safe mode can be included to detect process safety compliance, and can shut down operation of the heating unit if the processing chamber 16 is not properly set up. An alternative method of heater control which may be used utilizes a ramp control algorithm, which is described in the U.S. Pat. No. 5,968,587 to Jonathan Frankel, entitled "Systems and Methods for Controlling the Temperature of a Vapor Deposition Apparatus," and assigned to the assignee of the present invention.

A plasma control subroutine 150 comprises program code for setting low- and high-frequency RF power levels applied to the process electrodes in the processing chamber 16 and heater assembly 33 and for setting the low and high RF frequency employed. Like the previously described chamber component subroutines, plasma control subroutine 150 is invoked by chamber manager subroutine 145b. For embodiments including remote plasma system 34, shown in FIG. 2, plasma control subroutine 150 would also include program code for controlling the remote plasma generator.

Although the invention has been described in terms of specific embodiments, one skilled in the art will recognize that various wavelengths may be sensed to monitor characteristics to facilitate other films characterization in addition to the silicon containing film, such as dielectric films and refractory metal films. In addition, the present invention may be employed to dynamically control process conditions in response to the spectra sensed by the spectra analyzer via feedback control, adjusting parameters to maintain desired film characteristics and shutting down the process of unable to obtain desired film characteristics. Therefore, the scope of the invention should not be based upon the foregoing description. Rather, the scope of the invention should be determined based upon the claims recited herein, including the full scope of equivalents thereof.

What is claimed is:

1. A method for monitoring characteristics of films exposed to a source of light in a semiconductor processing chamber, said method comprising:
    sensing optical energy produced by said source of light, said optical energy having a plurality of spectral bands associated therewith;
    identifying a plurality of subsets, of said plurality of spectral bands, including information corresponding to the characteristics;
    measuring the characteristics as a function of said information, defining measured characteristics by sensing an intensity associated with each of said plurality of subsets, quantizing said intensity to produce a set of multiple quantizations, and summing said multiple quantizations, with each of said multiple quanitzations corresponding to one of said plurality of subsets.

2. The method as recited in claim 1 wherein identifying further includes identifying said plurality of subsets so that each of said plurality of subsets has an intensity associated therewith that varies as a function of said characteristics, defining a correlated intensity; and identifying a subgroup of said plurality of spectral bands that has an intensity associated therewith that varies independent of said characteristics, defining a disjunctive intensity; and measuring said characteristics further includes quantizing said disjunctive intensity, defining a disjunctive quantization, and quantizing the correlated intensity associated with each of said plurality of subsets, forming multiple correlated quantizations, with each of said multiple quantizations corresponding to one of said plurality of subsets and obtaining a ratio of said disjunctive quantization and each of said multiple correlated quantizations forming a set of multiple ratios and summing said multiple ratios in said set.

3. The method as recited in claim 2 wherein identifying said subset of said plurality of spectral bands further includes, for one of said plurality of subsets, defining a linear function to establish a linear relationship between said correlated quantizations and a subgroup of said multiple ratios and multiplying a subset of said multiple ratios by said linear function.

4. The method as recited in claim 1 further including varying said characteristics in response to said measured characteristics.

5. The method as recited in claim 1 wherein identifying said plurality of subsets further includes comparing said plurality of spectral bands with a baseline spectra and locating ranges of frequencies within said plurality of spectral bands that demonstrate a maximum variation with respect to said baseline spectra.

6. The method as recited in claim 1 wherein said characteristics are selected from a group consisting of film thickness, film stress, deposition rate and etch rate.

7. The method as recited in claim 1 wherein identifying said plurality of subsets further includes comparing said plurality of spectral bands with intensity information of a baseline spectra and including in said plurality of subsets ranges of frequencies of said spectral bands that demonstrate a maximum variation in intensity information with respect to said baseline spectra.

8. A method for monitoring characteristics of films exposed to a plasma in a semiconductor processing chamber:
    sensing optical energy produced by said plasma, said optical energy having a plurality of spectral bands associated therewith;
    identifying a plurality of subsets of said plurality of spectral bands each of which has an intensity associated therewith that varies in response to variations of said characteristics, defining a correlated intensity;

identifying a subgroup of said plurality of spectral bands that has an intensity associated therewith that varies minimally in response to variations of said characteristics, defining a disjunctive intensity; and measuring said characteristics, defining measured characteristics, by quantizing said disjunctive intensity, defining a disjunctive quantization, and quantizing the correlated intensity associated with each of said plurality of subsets, forming multiple correlated quantizations, with each of said multiple quantizations corresponding to one of said plurality of subsets and obtaining a ratio of said disjunctive quantization and each of said multiple correlated quantizations forming a set of multiple ratios and summing said multiple ratios in said set.

9. The method as recited in claim 8 wherein identifying said plurality of subsets further includes comparing said plurality of spectral bands with intensity information of a baseline spectra and including in said plurality of subsets ranges of frequencies of said spectral bands that demonstrateda maximum variation in intensity information with respect to said baseline spectra.

10. The method as recited in claim 9 wherein identifying said plurality of subsets further includes, for one of said plurality of subsets, defining a linear function to establish a linear relationship between said correlated quantizations and a subgroup of said multiple ratios, and multiplying a subset of said multiple ratios by said linear function.

11. The method as recited in claim 10 further including varying said characteristics in response to said measured characteristics.

12. The method as recited in claim 11 wherein said characteristics are selected from a group consisting of film thickness, film stress, deposition rate and etch rate.

13. A system for monitoring characteristics of films exposed to a plasma in a semiconductor processing chamber, said system comprising:

a detector in optical communication with said processing chamber to sense optical energy generated by said plasma, said optical energy having a plurality of spectral bands associated therewith;

a spectrum analyzer, in electrical communication with said optical detector, to resolve said spectral bands and produce information corresponding thereto;

a processor in electrical communication with said spectrum analyzer; and a memory in electrical communication with said processor, said memory comprising a computer-readable medium having a computer-readable program embodied therein, said computer-readable program including a first set of instructions to cause said processor to operate on said information and identify a plurality of subsets of said plurality of spectral bands having data corresponding to said characteristics; and a second set of instructions to control said processor to measure said characteristics as a function of said information by sensing an intensity associated with each of said plurality of subsets, quantizing said intensity to produce a set of multiple quantizations, and summing said multiple quantizations, with each of said multiple quantizations corresponding to one of said plurality of subsets.

14. The system as recited in claim 13 wherein said memory further includes a third set said of instructions to identify a subgroup of said plurality of spectral bands having data associated therewith, with substantially all of the data associated with the spectral bands of said subgroup being independent of said characteristics, and a fourth set of instructions to measure said characteristics as a function of both said information and said data.

15. The system as recited in claim 13 wherein said first set of instructions includes a subroutine to identify a subgroup of said plurality of spectral bands having an intensity associated therewith that varies as a function of said characteristics.

16. The system as recited in claim 13 wherein said first set of instructions includes a first subroutine to identify a first portion of said plurality of spectral bands having a first intensity associated therewith that varies as a function of said characteristics and identify a second portion of said plurality of spectral bands having a second intensity associated therewith that is substantially independent of said characteristics, wherein said second set of instruction further includes a second subroutine to measure said characteristics as a function of both said information and data by quantizing said first and second intensity, defining first and second quantizations and obtaining a ratio of said first and second quantizations.

17. The system as recited in claim 13 wherein said first set of instructions further includes a subroutine to compare said plurality of spectral bands with a baseline spectra and locating a subset of said plurality of spectral bands that demonstrate a maximum variation with respect to said baseline spectra.

18. A method for monitoring characteristics of films exposed to a source of light in a semiconductor processing chamber, said method comprising:

sensing optical energy produced by said source of light, said optical energy having a plurality of spectral bands associated therewith;

identifying a subset of said plurality of spectral bands, including information corresponding to said characteristics;

obtaining a sequence of measurements of said subset at differing intervals of time, defining a sequence of measured intensity data;

normalizing said sequence of measured intensity data to produce a normalized sequence of intensity data;

obtaining a linear function from said normalized sequence of intensity data and said sequence of measured data; and measuring said characteristics as a function of a product of said linear function and a sum of the data in said normalized sequence of intensity data.

19. The method as recited in claim 18 wherein identifying said subset further includes identifying first and second sub-bands of said plurality of spectral bands, with said first sub-band having an intensity associated therewith that varies in response to variations in said characteristics, defining said measured intensity data and said second subset having an intensity associated therewith that varies substantially independently of variations in said characteristics, defining disjunctive intensity data; and normalizing said sequence of measured intensity data further includes obtaining, for each of said differing intervals of time, a ratio of said measured intensity data and said disjunctive intensity data, to define said normalized sequence of intensity data.

20. The method as recited in claim 18 wherein obtaining said linear function further includes mapping said measured intensity data and said normalized sequence of intensity data to a graph and fitting a curve to said graph that most closely fits a linear function.

* * * * *